United States Patent

Hagen et al.

(10) Patent No.: US 6,720,455 B2
(45) Date of Patent: Apr. 13, 2004

(54) PROCESS FOR THE PRODUCTION OF POLYISOCYANATES OF THE DIPHENYLMETHANE SERIES WITH A REDUCED COLOR VALUE

(75) Inventors: Torsten Hagen, Düsseldorf (DE); Friedhelm Kämper, Krefeld (DE); Daniel Koch, Duisburg (DE); Heinz-Herbert Müller, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 7 days.

(21) Appl. No.: 10/224,003

(22) Filed: Aug. 20, 2002

(65) Prior Publication Data

US 2003/0045745 A1 Mar. 6, 2003

(30) Foreign Application Priority Data

Aug. 24, 2001 (DE) .......................... 101 41 620

(51) Int. Cl.⁷ ..................... C07C 209/84; C07C 263/10
(52) U.S. Cl. ..................... 564/333; 560/347; 564/330; 564/307
(58) Field of Search .......................... 560/347; 564/307, 564/330, 333

(56) References Cited

U.S. PATENT DOCUMENTS 5,310,769 A   5/1994   König et al. ............. 521/163
5,994,579 A   11/1999  Torrel et al. ............. 560/347
6,031,136 A   2/2000   Renbaum et al. .......... 564/333
6,140,382 A   10/2000  Gallus et al. ............ 521/155

FOREIGN PATENT DOCUMENTS

CA   2320477    8/1999
DE   42 32 769  8/1994

OTHER PUBLICATIONS

Chem. Soc. Rev. 3(2), (month unavailable) 1974, pp. 209–230, H.J. Twitchet, "Chemistry of the Production of Organic Isocyanates".

Kirk–Othmer Encycl. Chem. Technol., 3³. ed.., New York, 2, (month unavailable) 1978, pp. 338–348, W.H. Moore, Methylenedianiline.

Database CA Online! Chemical Abstracts Service, Columbus, Ohio US; retrieved from STN.

Primary Examiner—Peter G O Sullivan
(74) Attorney, Agent, or Firm—Joseph C. Gil; Lyndanne M. Whalen

(57) ABSTRACT

Polyisocyanates of the diphenylmethane series are produced by a) reacting aniline and formaldehyde in the presence of an acidic catalyst to produce a polyamine, b) neutralizing the reaction mixture from step a) with a base at a temperature of more than 110° C. or neutralizing the reaction mixture from step a) with a base and heating the neutralized mixture to a temperature of more than 110° C., and c) phosgenating the polyamine from step b) to convert it to the corresponding polyisocyanate.

6 Claims, No Drawings

PROCESS FOR THE PRODUCTION OF POLYISOCYANATES OF THE DIPHENYLMETHANE SERIES WITH A REDUCED COLOR VALUE

BACKGROUND OF THE INVENTION

The invention relates to a process for the production of polyamines of the diphenylmethane series and to a process for the production of polyisocyanates of the diphenylmethane series with a reduced color value. These polyisocyanates are obtained by reacting the corresponding polyamines of the diphenylmethane series with phosgene.

Polyisocyanates of the diphenylmethane series are understood to mean isocyanates and mixtures of isocyanates of the following type:

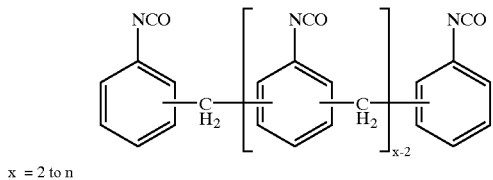

$x = 2$ to $n$

Similarly, polyamines of the diphenylmethane series are understood to mean compounds and mixtures of compounds of the following type:

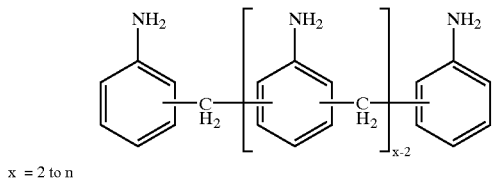

$x = 2$ to $n$

The industrial production of isocyanates by the reaction of amines with phosgene in solvents is known and is described in detail in the literature (See, e.g., Ullmanns Enzyklopädie der technischen Chemie, $4^{th}$ edition, volume 13, pages 347–357, Verlag Chemie GmbH, Weinheim, 1977.). Based on this process, a mixture of polyisocyanates is produced. Such polyisocyanates are used as the polyisocyanate component in the production of polyurethane foams and other polyurethane plastics produced by the polyaddition process.

It is generally known that undesirable coloring components are also formed in this process. These coloring components are retained upon processing to produce polyurethane foams or other polyurethane plastics. Although the inherent color of the polyisocyanate polyaddition products does not have a negative effect on their mechanical properties, substantially colorless products are desired by the consumer. The absorbance at different wavelengths serves as a measure of the discoloration of the polyisocyanate.

For some time, therefore, the reduction of the color values of polyisocyanates of the diphenylmethane series has been the goal of numerous experiments and works that are described in the literature. For example, DE-A1-4208359 describes the treatment of isocyanates with hydrogen in the presence of supported catalysts. DE-A1-4232769 describes the addition of amines, ureas and antioxidants to the isocyanate. DE-A1-19815055 teaches that the color of polyisocyanates of the diphenylmethane series may be improved by irradiation with light over a prolonged period. DE-A1-19804915 describes the brightening of polyisocyanates of the diphenylmethane series by a complicated time- and temperature-stepped addition of formaldehyde to the polyamine step to produce an amine which is then converted to the desired isocyanate by phosgenation.

A disadvantage of all of these procedures is that they are technically complex and/or require the use of non-isocyanate auxiliary substances or are of low efficiency.

SUMMARY OF THE INVENTION

The object of the present invention was therefore to provide a technically simple and safe process for the production of polyisocyanates of the diphenylmethane series with low color values.

The object of the present invention was also to provide a simple process for the production of polyamines of the diphenylmethane series from which polyisocyanates of the diphenylmethane series with low color values can be produced by phosgenation.

These objects are achieved by
a) reacting aniline and formaldehyde in the presence of an acidic catalyst to produce a polyamine, and
b) neutralizing the reaction mixture from step a) with a base either at a temperature of more than 110° C. or by neutralizing the reaction mixture from step a) and heating the neutralized reaction mixture to a temperature of more than 110° C. after neutralization.

These objects are also achieved by a process for the production of polyisocyanates of the diphenylmethane series in which
a) aniline and formaldehyde are reacted in the presence of an acidic catalyst to produce a polyamine,
b) the reaction mixture from step a) is neutralized with a base either at a temperature of more than 110° C. or the reaction mixture from step a) is neutralized and then heated to a temperature of more than 110° C. after neutralization, and
c) phosgenating the polyamine produced in b) is phosenated to produce the corresponding polyisocyanate.

DETAILED DESCRIPTION OF THE INVENTION

The processes for the production of polyamines and polyisocyanates in accordance with the present invention can be carried out both continuously and non-continuously.

Polyisocyanates with low color values can be produced by the process according to the invention. Color value here is understood to mean the measured absorbance of a solution of polyisocyanate in monochlorobenzene, containing 2 wt. % polyisocyanate, in a layer thickness of 10 mm and at room temperature, against monochlorobenzene at defined wavelengths.

The polyamine or mixture of polyamines of the diphenylmethane series used in the process of the present invention is obtained by condensation of aniline and formaldehyde in the presence of an acidic catalyst. (See, e.g., H. J. Twitcheft, Chem. Soc. Rev. 3(2), 209 (1974), W. M. Moore in: Kirk-Othmer Encycl. Chem. Technol., $3^{rd}$ ed., New York, 2, 338–348 (1978).) It is of no importance to the process of the present invention whether aniline and formaldehyde are first mixed in the absence of the acidic catalyst and the acidic catalyst is then added or whether a mixture of aniline and acidic catalyst is reacted with formaldehyde.

Suitable polyamines and mixtures of polyamines of the diphenylmethane series are conventionally obtained by condensation of aniline and formaldehyde in a molar ratio of aniline to formaldehyde of from 20 to 1.6, preferably from 10 to 1.8, and a molar ratio of aniline to acidic catalyst of from 20 to 1, preferably from 10 to 2.

Formaldehyde is conventionally used in industry as an aqueous solution. However, other compounds providing methylene groups can also be used, such as e.g. polyoxymethylene glycol, para-formaldehyde or trioxane.

Strong organic and preferably inorganic acids have proven suitable as acidic catalysts. Examples of suitable acids are hydrochloric acid, sulfuric acid, phosphoric acid and methanesulfonic acid. Hydrochloric acid is preferably used.

In a preferred embodiment of the process, aniline and acidic catalyst are first combined. In another step, this mixture is mixed with formaldehyde in a suitable manner at temperatures between 20° C. and 100° C., preferably at 30° C. to 70° C., optionally after dissipation of heat, and then subjected to a preliminary reaction in a suitable residence-time apparatus. The preliminary reaction takes place at temperatures between 20° C. and 100° C., preferably in the temperature range of from 30° C. to 80° C. Following the mixing and preliminary reaction, the temperature of the reaction mixture is brought, stepwise or continuously and optionally under excess pressure, to a temperature of from 100° C. to 250° C., preferably from 100° C. to 180° C., most preferably to a temperature of from 100° C. to 160° C.

In another embodiment of the process, however, it is also possible to mix aniline and formaldehyde first in the absence of the acidic catalyst at a temperature in the range of from 5° C. to 130° C., preferably from 40° C. to 100° C., most preferably from 60° C. to 85° C., and to react them. This leads to the formation of condensation products of aniline and formaldehyde (a so-called "aminal"). Following the aminal formation, water present in the reaction mixture can be removed by phase separation or other appropriate process steps, e.g. by distillation. The condensation product is then mixed with the acidic catalyst in a suitable manner in another process step and subjected to a preliminary reaction in a residence-time apparatus at a temperature of from 20° C. to 100° C., preferably from 30° C. to 80° C. The temperature of the reaction mixture is then brought, stepwise or continuously and optionally under excess pressure, to a temperature of from 100° C. to 250° C., preferably from 100° C. to 180° C., most preferably to a temperature of from 100° C. to 160° C.

The reaction of aniline and formaldehyde in the presence of an acidic catalyst to produce a polyamine of the diphenylmethane series can take place in the presence of other substances (e.g. solvents, salts, organic and inorganic acids).

To work up the acidic reaction mixture, the reaction mixture is neutralized with a base. According to the prior art, the neutralization is conventionally conducted at temperatures of, e.g., from 90 to 100° C. (H. J. Twitcheft, Chem. Soc. Rev. 3(2), 223 (1974)). The hydroxides of the alkali and alkaline earth elements are examples of suitable bases. Aqueous NaOH is preferably used.

In the process according to the present invention, the neutralization of the acidic reaction mixture is performed at a temperature of more than 110° C., typically at a temperature in the range of from 111° C. to 300° C., preferably at 115° C. to 200° C., more preferably at 120° C. to 180° C., and most preferably 130 to 160° C. Alternatively, the neutralization may be performed at a temperature less than 110° C. and the neutralized reaction mixture may then be heated to a temperature of more than 110° C., typically from 111° C. to 300° C., preferably from 115° C. to 200° C., more preferably from 120° C. to 180° C., and most preferably from 130 to 160° C.

The neutralization may be conducted, for example, by mixing the acidic reaction mixture of the aniline/formaldehyde condensation with the base and feeding the resultant mixture into a residence-time apparatus (e.g., a stirred vessel, a stirred vessel cascade, a flow pipe, or a forced circulation reactor). In a suitable residence-time apparatus (e.g., stirred vessel), mixing of the acidic condensation mixture and the base can also take place directly in the residence-time apparatus.

The neutralized reaction mixture is preferably held at a temperature of more than 110° C. for a residence time of $\geq 0.1$ min, preferably from 0.1 to 180 min, more preferably from 2 to 120 min, most preferably from 10 to 60 min.

To adjust the mixture temperature to a temperature suitable for conducting the process of the present invention, it may be necessary to introduce or dissipate heat. This depends particularly on the desired temperature at which the neutralization is to take place, and also on the heat liberated during neutralization, the temperature of the acidic condensation mixture and the temperature of the base or base solution used. To prevent boiling below the desired neutralization temperature, the process may have to be carried out under increased pressure.

The base used for neutralization is used in a quantity of more than 100%, preferably from 101 to 140%, most preferably from 105 to 120% of the quantity stoichiometrically required to neutralize the acidic catalyst used. The effect of neutralization at elevated temperature on the color of the polyisocyanates of the diphenylmethane series is reinforced if sufficiently thorough mixing of the organic and aqueous phases is ensured in the neutralization residence-time vessel. This can be achieved by using any of the methods known in the art, e.g. by static or dynamic mixers or by producing turbulence.

Following neutralization, the organic phase is conventionally separated from the aqueous phase by appropriate processes (e.g., phase separation in a separatory funnel). This separation of organic and aqueous phases can take place at the same temperature at which the neutralization of the acidic rearrangement mixture took place. The product-containing organic phase remaining after separating off the aqueous phase is conventionally subjected to further working-up steps (e.g., washing) and then freed from excess aniline and other substances present in the mixture (e.g. other solvents) by suitable physical methods of separation such as distillation, extraction or crystallization.

The polyamine of the diphenylmethane series (crude MDA) thus obtained is converted to the corresponding isocyanate by any of the known methods with phosgene in an inert organic solvent. The molar ratio of crude MDA to phosgene is usefully calculated such that from 1 to 10 moles, preferably from 1.3 to 4 moles of phosgene are present in the reaction mixture per mole of $NH_2$ group. Chlorinated, aromatic hydrocarbons, such as monochlorobenzenes, dichlorobenzenes, trichlorobenzenes, the corresponding toluenes, xylenes and chloroethylbenzene are suitable inert solvents. Monochlorobenzene, dichlorobenzene and mixtures of these chlorobenzenes are particularly useful inert organic solvents. The quantity of solvent is preferably calculated such that the reaction mixture has an isocyanate content of from 2 to 40 wt. %, preferably between 5 and 20 wt. %, based on the total weight of the reaction mixture. On completion of the phosgenation, the excess phosgene, the inert organic solvent, the HCl formed and any mixtures thereof are separated from the reaction mixture by, for example, distillation.

The crude MDI produced by the process of the present invention possesses clearly reduced color. However, further analytical differences can be detected in the MDI produced (e.g., an increased content of isocyanate groups.)

Having thus described the invention, the following Examples are given as being illustrative thereof.

EXAMPLES

Example 1

Comparative Example 707.6 g of aniline and 563.6 g of a 32.0% aqueous formaldehyde solution were added dropwise, at the same time, to 410 g of aniline at 80° C. within 20 min. After the addition, stirring was continued for 10 min and a phase separation was then performed at 70–80° C. A quantity of 284.5 g of the organic phase was brought to a temperature of 35° C. and then the remaining organic phase and 341.9 g of a 32.0% aqueous hydrochloric acid were added at this temperature within 29 min. On completion of the addition and after a further 30-minute period of stirring at this temperature, the mixture was heated to 60° C. for 10 min and kept at this temperature for 30 min. It was then heated to reflux temperature within 30 min and stirred under reflux for 10 h. 154.3 g of a 49.6% aqueous sodium hydroxide solution and 213 ml of boiling water were added to 815 g of the acidic rearrangement mixture thus obtained. After stirring under reflux for 15 min, phase separation was performed at 80–90° C. and the organic phase was washed twice more with 638 ml of boiling water each time. The organic phase was then freed from excess aniline under reduced pressure. 50 g of the polyamine thus obtained were dissolved in 255 ml of chlorobenzene, heated to 55° C. and added within 10 s to a solution of 105 g of phosgene in 310 ml of chlorobenzene at a temperature of 0° C., stirring vigorously. The suspension was heated to 100° C. within 45 min while passing through phosgene, and then heated to reflux temperature for 10 min. After an additional 10 minutes at this temperature, the solvent was distilled off under reduced pressure to a bottom temperature of 100° C. The crude isocyanate was then heated in distillation apparatus under a pressure of 4–6 mbar by a heating bath heated to 260° C. to the first product transition and then cooled to room temperature within 5 min. 1.0 g of the isocyanate thus obtained was dissolved in chlorobenzene and diluted to 50 ml with chlorobenzene. The solution thus obtained possessed an absorbance of 0.193 against chlorobenzene at a wavelength of 430 nm, in a layer thickness of 10 mm and at room temperature.

Example 2

According to the Invention 699 g of an acidic rearrangement mixture corresponding to that produced in Example 1 were neutralized with 132.4 g of 49.6% aqueous sodium hydroxide solution with the addition of 60.8 g of water. The reaction mixture was transferred into a pressure vessel and stirred for 3 h at 160° C. under inherent pressure. The phases were then separated and the organic phase was purified in the same manner as is described in Example 1. The resulting polyamine was converted to the corresponding isocyanate as in Example 1. The absorbance at 430 nm of the isocyanate was measured by the same method as that described in Example 1. The absorbance of the product isocyanate was 0.163.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

Example 3

According to the Invention 403 g of an acidic rearrangement mixture corresponding to that produced in Example 1 were neutralized with 76 g of 50% aqueous sodium hydroxide solution with the addition of 105 g of water. The reaction mixture was transferred into a pressure vessel and stirred for 15 min at 160° C. under inherent pressure. The phases were then separated and the organic phase was purified in the same manner as is described in Example 1. The resulting polyamine was converted to the corresponding isocyanate as in Example 1. The absorbance at 430 nm of the isocyanate was measured by the same method as that described in Example 1. The absorbance of the product was 0.164.

What is claimed is:

1. Process for the production of a polyamine of the diphenylmethane series comprising
    a) reacting aniline and formaldehyde in the presence of an acidic catalyst to produce a polyamine and
    b) (i) neutralizing the reaction mixture from step a) with a base at a temperature of more than 110° C. or (ii) neutralizing the reaction mixture from step a) with a base and heating the neutralized mixture to a temperature of more than 110° C.

2. The process of claim 1 in which the neutralization is performed at a temperature of from 120 to 180° C.

3. The process of claim 1 in which aqueous NaOH is used as the base.

4. A process for the production of a polyisocyanate of the diphenylmethane series comprising
    a) reacting aniline and formaldehyde in the presence of an acidic catalyst to produce a polyamine,
    b) (i) neutralizing the reaction mixture from step a) with a base at a temperature of more than 110° C. or (ii) neutralizing the reaction mixture from step a) with a base and heating the neutralized mixture to a temperature of more than 110° C., and
    c) phosgenating the polyamine from step b) to produce the corresponding polyisocyanate.

5. The process of claim 4 in which the neutralization is performed at a temperature of 120 to 180° C.

6. The process of claim 4 in which aqueous NaOH is used as the base.

* * * * *